United States Patent [19]

Sargeant et al.

[11] 4,439,189
[45] Mar. 27, 1984

[54] PLEURAL DRAINAGE SYSTEM

[75] Inventors: John E. Sargeant, Los Alamitos; Jack L. Hoffa, Brea, both of Calif.

[73] Assignee: Bentley Laboratories, Inc., Irvine, Calif.

[21] Appl. No.: 274,788

[22] Filed: Jun. 18, 1981

[51] Int. Cl.³ ............................................. A61M 1/00
[52] U.S. Cl. .................................... 604/317; 604/321; 137/205
[58] Field of Search ............... 128/276, 760, 762, 767, 128/760, 762, 767; 137/205; 604/317, 319–321

[56] References Cited

U.S. PATENT DOCUMENTS

| | | | |
|---|---|---|---|
| 3,363,626 | 1/1968 | Bidwell et al. | 128/276 |
| 3,363,627 | 1/1968 | Bidwell et al. | 128/276 |
| 3,559,647 | 2/1971 | Bidwell et al. | 128/276 |
| 3,683,913 | 8/1972 | Kurtz et al. | 128/276 |
| 3,750,692 | 8/1973 | Tibbs | 137/205 |
| 4,018,224 | 4/1977 | Kurtz et al. | 128/276 |
| 4,178,934 | 12/1979 | Forman | 128/762 |
| 4,312,351 | 1/1982 | Kurtz et al. | 128/276 |
| 4,372,336 | 2/1983 | Cornell et al. | 604/319 |

OTHER PUBLICATIONS

Henry J. Heimlich, M.D., "Understanding Chest Drainage by Understanding Breathing", *Hospital Care*, Oct. 1970, vol. 1, No. 3.
Margo Saum, RN, "Taking the Mystery Out of Chest Tubes", *AORN Journal*, Jul. 1980, vol. 32, No. 1, p. 86.
Clinical Aspects of Chest Drainage, Book 2, Argyle, Division of Sherwood Medical.

*Primary Examiner*—C. Fred Rosenbaum
*Assistant Examiner*—J. Kruter
*Attorney, Agent, or Firm*—Lyon & Lyon

[57] ABSTRACT

A system for draining pleural cavities. A container having a plurality of cavities is employed with a vacuum source and an inlet from the patient. In the first cavity, a port is defined to limit the liquid contained therein. This port opens into a second cavity for collection of drained fluids. A vacuum regulator mechanism is incorporated at one end of the container to prevent injury to the patient. Thus, a water seal is defined about the inlet tube. A separate cavity collects drained fluids and a third area provides vacuum control.

2 Claims, 11 Drawing Figures

PLEURAL DRAINAGE SYSTEM

BACKGROUND OF THE INVENTION

The field of the present invention is drainage systems for pleural cavities.

Air and liquid can enter the pleural cavity through a number of abnormal sources. The chest wall may have been punctured acidentally or through surgery, or the lung may have been punctured or cut. In either case, drainage of the pleural cavity is required. This need to drain the pleural cavity may exist for some time, requiring a drainage mechanism that may be left unattended with safety.

To provide a safe drainage mechanism which may be left on the patient, several features must be considered. First, it is desirable to have a water seal between the link to the pleural cavity and either atmosphere or a vacuum source. Even so, under extreme conditions when the plueral cavity for some reason has a lower pressure than the drainage unit, it is desirable to prevent liquid from flowing back up into the pleural cavity. Vacuum is believed to be beneficial for improving the drainage conditions. However, normal hospital vacuum sources are often not sufficiently reliable to ensure against harmful vacuum levels. Consequently, a reliable vacuum regulator is also advantageous to such a system. Finally, it is advantageous to have a system for collecting the drained fluid so that the amount and nature of this fluid can be monitored.

A number of different systems have developed for pleural drainage. These systems have been classified in an historical sense based on the number of bottles employed in the system. A one-bottle water seal chest drainage system includes a single tube from the patient through a stopper and into a bottle. The tube extends to almost the bottom of the bottle. A vacuum outlet also extends through the stopper into the upper end of the bottle. The bottle is then primed with liquid to create a water seal over the end of the tube from the patient. The one-bottle system is disadvantageous because there is no control over the level of vacuum, there is no control over fluid returning to the pleural cavity, and the amount of head in the bottle cannot be controlled as fluid from the patient causes the water level to rise.

In recognition of certain of the problems of the one-bottle system, a two-bottle system was developed which had a drainage tube from the patient into a collecting chamber. The tube remained above the water level and no water seal was formed in the first bottle. A second tube ran from the first bottle deep into a second bottle. The second bottle was filled over the end of the connecting tube to create a water seal. Another tube then lead from the second bottle to a vacuum chamber. This device also did not protect the patient from excessive vacuum. However, fluid could not return to the pleural cavity and the level of the drainage did not affect the vacuum experienced by the patient.

A classic three-bottle system was developed which incorporated the same mechanism as the two-bottle system with the addition that the second bottle was not hooked to a vacuum source but rather to a third bottle. The third bottle employed a simple vacuum regulator incorporating a tube extending from atmosphere outside the bottle to a position adjacent the bottom. Water was then added to the bottom to create a specific head. Vacuum was then limited by the head in the third bottle. This device eliminated the majority of the difficulties with the simpler systems. However, the amount of tidal air in the first bottle was generally significant in order to provide sufficient capacity for fluid collection. This is considered objectionable by many doctors who preferred the water seal at the tube leading from the patient. For example, an air leak in the fluid collection bottle could pull air into the pleural cavity in a three-bottle system.

Illustrative of the nature of current designs of three bottle systems is a patent to R. E. Bidwell et al., U.S. Pat. No. 3,363,627. This patent is incorporated herein by reference as illustrative of the prior art.

Thus, a number of problems have been resolved with variations in the types of pleural draining systems available. However, certain of the improvements have eliminated beneficial features of the earlier devices. Consequently, the need has long been established for improving on current systems.

SUMMARY OF THE INVENTION

The present invention is directed to a pleural drainage system. This system incorporates a water seal at the outlet of the tube from the patient to reduce tidal volume. At the same time, a mechanism is provided which prevents fluid return to the pleural cavity even under adverse pressure conditions. The difficulties of the one-bottle system where the head in the first water seal could not be controlled are advantageously overcome by the present invention where a spillway limits the head.

Beyond the systems advantages of the present invention certain practical advantages provide additional aspects of the present invention. The mechanism is designed to not lose its prime when tipped on its side. The water forming the water seal is retained by the configuration of the device and the seal is re-established when the device is rightened. The device is also configured such that it has a wide base to resist such tipping. In spite of the wide base, a first compartment for the collection of fluids is designed with a reduced horizontal cross-sectional area. Thus, greater accuracy is achieved in measuring the volume of drained fluid collected. The drainage chamber is also designed to be progressively filled over partitions in order that a more accurate reading in the change in drained volume is available. The device is also advantageously arranged so that large volumes of collected fluids can be drained from the device without the danger of creating an excessive level of vacuum in the pleural cavity resulting from such drainage. This is accomplished by placing the collection cavity in direct communication with the vacuum source as well as the vacuum regulator. Also, the device has been designed to keep bubbling noises to a minimum. Such noises have been found to have a negative psychological impact on the patient.

Accordingly, it is an object of the present invention to provide an improved pleural drainage system. Other and further objects and advantages will appear hereinafter.

DETAILED DESCRIPTION OF THE PREFERRED EMBODIMENT

Figure 1:
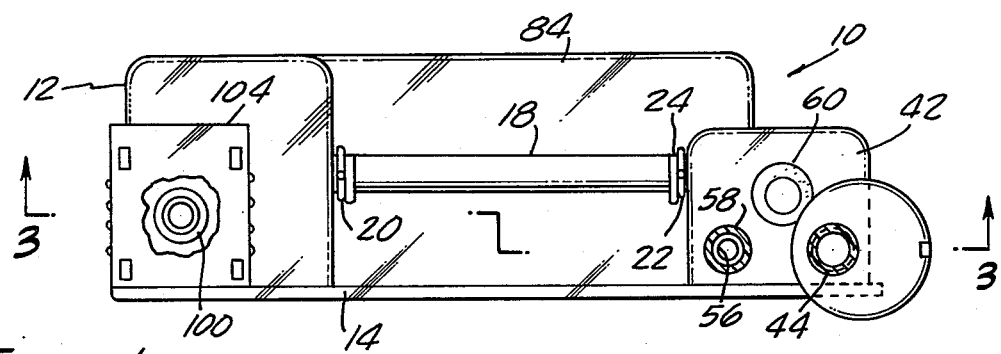
FIG. 1 is a plan view of the device of the present invention.

Turning in detail to the drawings, the preferred embodiment is designed as a unitary container 10 of plastic having a molded body 12 and a front plate 14. The front plate 14 is generally planar and is bonded to the molded body 12 to provide an air tight joint. The molded body 12 is divided by means of internal partitions into a plurality of cavities having a variety of functions. The front plate 14 also forms a seal with these partitions to complete each cavity. The plastic selected for construction of the container 10 is preferably clear, at least for the front plate 14, in order that drainage can be visually monitored. Graduations 16 are provided on the front plate 14 for easy measurement of the volumes of liquid in the several compartments of the container 10. A handle 18 is provided at the upper portion of the container 10 for easy carrying. Hooks 20 and 22 are wrapped about the handle 18 to provide easy attachment to a bed or the like. The handle 18 includes ribs 24 to retain the hooks 20 and 22 in position at the outer ends of the handle 18. The handle 18 is U-shaped in cross section for easy molding.

Turning then to the interior of the container 10, a first cavity 26 is provided at one upper corner of the container 10. To define the cavity, a bottom 28 and a wall 30 combine with the sidewalls 32, 34, 36 and the front plate 14 to define this first cavity 26.

Figure 8:
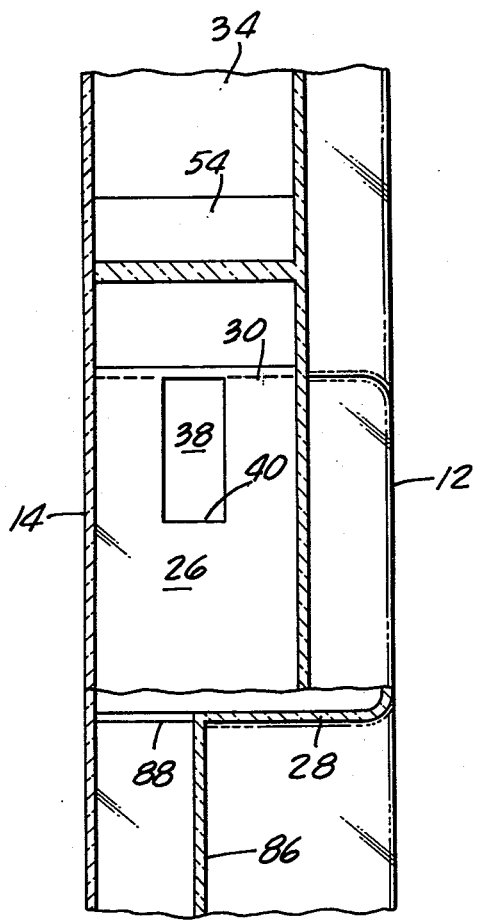
FIG. 8 is a cross-sectional side view taken along line 8—8 of FIG. 3.

The wall 30 has a port 38 therethrough. This port is located at and above a first level defined by the edge of the wall at 40. The port 38 is of sufficient area to allow unrestricted fluid communication above the first level defined by edge 40. That is to say, the size of the port 38 is large enough to accommodate all of the drainage which may be anticipated from the patient and also allow air communication between the various parts of the container 10. The port 38 is also defined in the preferred embodiment in the wall 30 spaced from the walls defined by the front plate 14 and back wall 36. This arrangement is best seen in FIG. 8.

The location and size of the port 38 creates a first fixed volume defined by the area of the first cavity 26 below the first level of edge 40. The head of liquid contained within this first cavity 26 cannot rise above this first level without draining from the cavity. Thus, a fixed head and a fixed volume of liquid are defined in the first cavity 26 by the port 38. The spacing of the port 38 from the plate 14 and back wall 36 is intended to prevent loss of prime when the container 10 is laid on its side. The volume of liquid contained within the first cavity 26 will simply flow to either the front wall 14 or back wall 36 and not rise over the sides of the port 38. When righted, the liquid will return to the lower part of the cavity 26 to re-establish a water seal.

Extending through the top 42 is an inlet tube 44. The inlet tube 44 extends to a second level within the first cavity 26. This level is below the first level established at edge 40. The outlet of the tube 44 is spaced from the bottom 28 to ensure unrestricted flow. The tube 44 is also of sufficient diameter to allow free passage of clotted blood.

Figure 3:
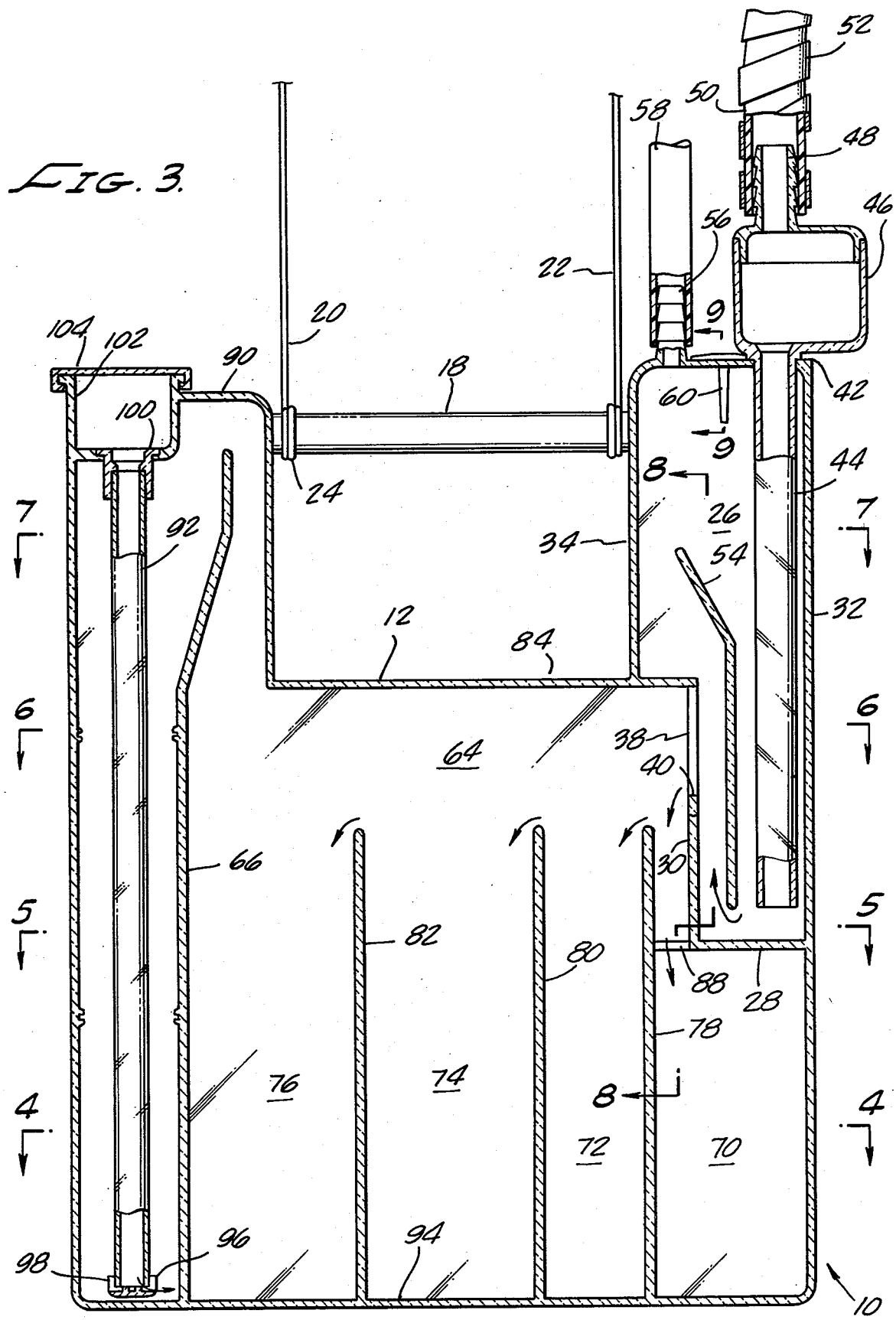
FIG. 3 is a cross-sectional elevation taken along line 3—3 of FIG. 1.
Figure 4:
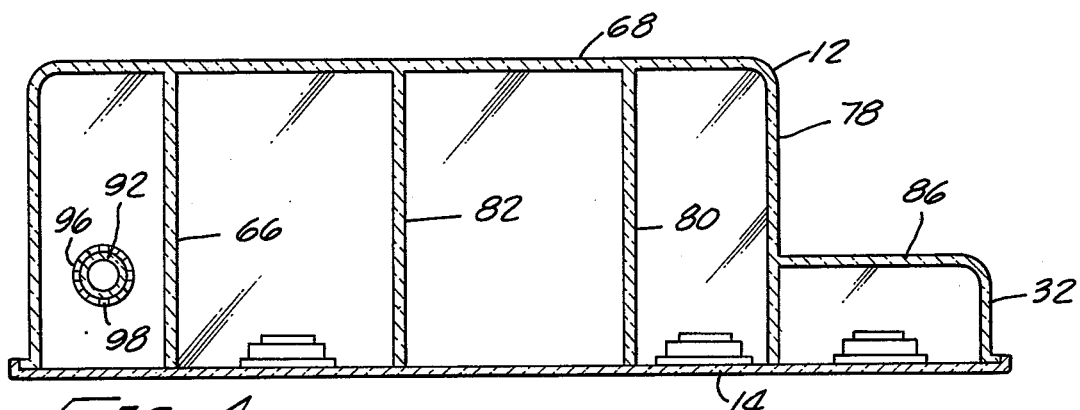
FIG. 4 is a cross-sectional plan view taken along line 4—4 of FIG. 3.
Figure 5:
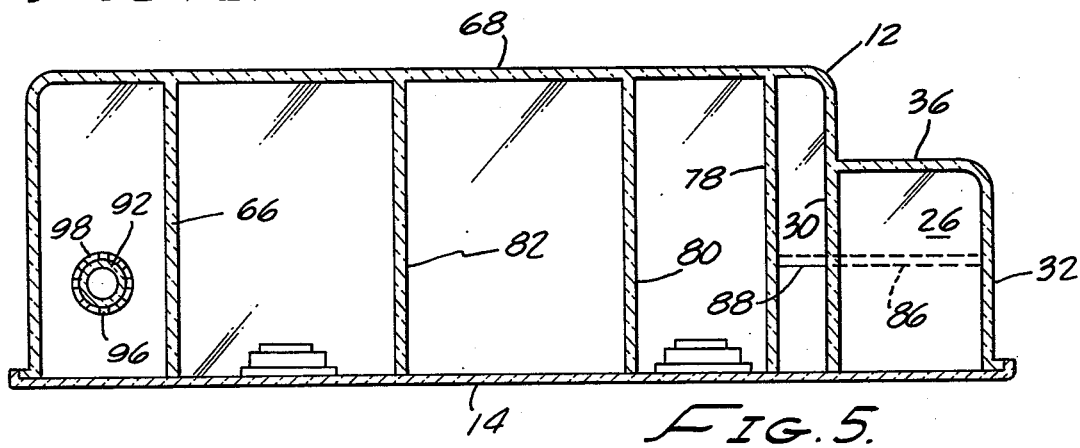
FIG. 5 is a cross-sectional plan view taken along line 5—5 of FIG. 3.
Figure 6:
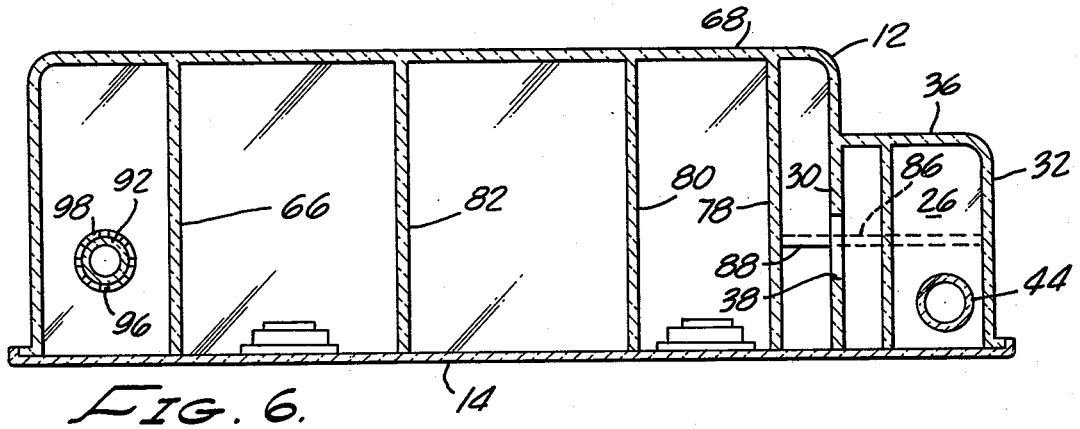
FIG. 6 is a cross-sectional plan view taken along line 6—6 of FIG. 3.
Figure 7:
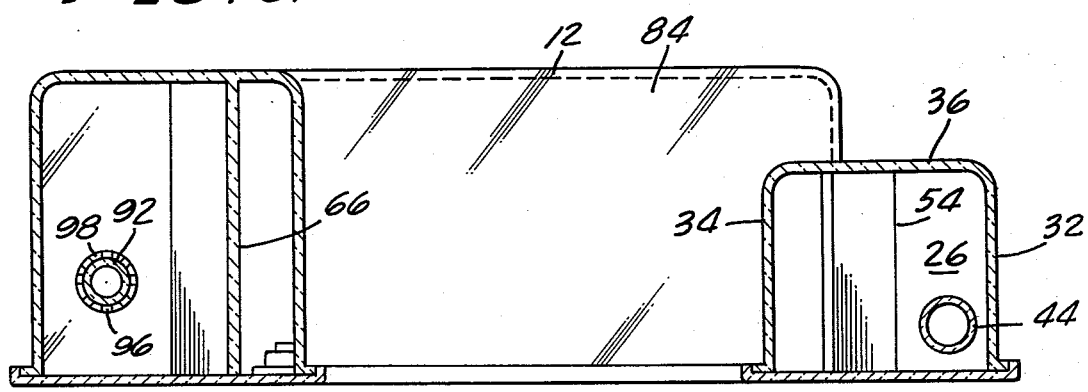
FIG. 7 is a cross-sectional plan view taken along line 7—7 of FIG. 3.

Above the first cavity 26, the tube expands to a rigid container 46. This container 46 is conveniently assembled in two parts, as can be seen in FIG. 3, and includes a fitting 48 for accepting a tube. The container 46 defines a third cavity having a volume which is greater than the volume defined below the first level in the first cavity 26. Thus, if pressure is greater in the container 10 than in the inlet, the liquid within the first cavity 26 will rise in the tube 44 and into the third cavity defined by the container 46. Once this liquid has risen into the container 46, air may then flow up through the tube 44, through the unrestricted area of the container 46, and through the fitting 48. In this way, fluid cannot be drawn back into the pleural cavity.

The tube 50 associated with the fitting 48 extends to the pleural cavity of the patient. To avoid tube kinking, a plastic strip 52 is wound about the tube 50 to provide a spreading of the stress to prevent kinks.

A baffle 54 is positioned in the first cavity 26 between the outlet of the tube 44 and the port 38. This baffle is designed to prevent loss of prime resulting from violent bubbling from the tube 44. The liquid carried with the bubbling will rise up on the tube side of the baffle 54 and return rather than be blown through the port 38.

Figure 9:
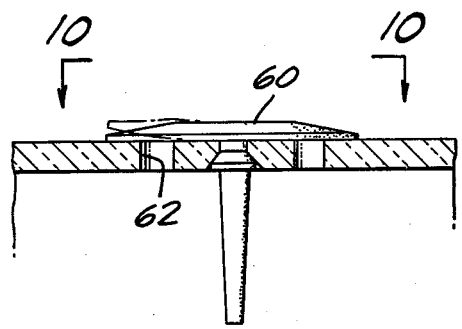
FIG. 9 is a cross-sectional side view taken along line 9—9 of FIG. 3.
Figure 10:
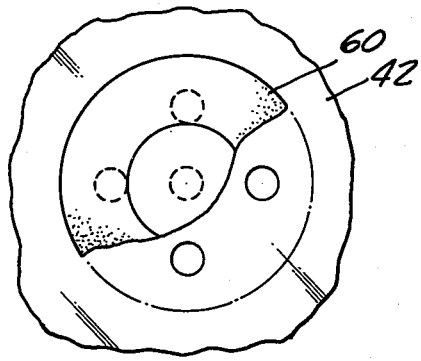
FIG. 10 is a top view taken along line 10—10 of FIG. 9.

Also located in the top 42 is a fitting 56 which is hooked to a vacuum source tube 58. Also located in the top 42 is an umbrella valve 60 as best seen in FIGS. 9 and 10. The umbrella valve 60 is of resilient material to allow passage of over-pressure through vents 62. Thus, any overpressure from the patient will be vented from the container 10 if vacuum line is blocked or clamped. The vacuum outlet at fitting 56 and the pressure relief of the umbrella valve 60 are located above the first level defined by the edge 40 of the wall 30. As the port 38 is defined such that it cannot be filled with liquid, vacuum communication extends from the first cavity 26 into the remainder of the container 10.

The first cavity 26 is in communication through port 38 with a second cavity 64 defined in the container 10. This cavity extends from the sidewall 32 over to a partition 66 between the front plate 14 and a back wall 68. This second cavity 64 is divided into a plurality of separate chambers 70, 72, 74 and 76 by partitions 78, 80 and 82. The partitions 78, 80, and 82 do not extend up to the top 84 of the second cavity 64 so that liquid can pass over each of the partitions to sequentially fill each chamber.

The first chamber 70 has a separate back wall 86 which is significantly closer to the front plate 14 than the back wall 68. In this way, the cross-sectional area of the chamber 70 is significantly reduced. This provides more accurate reading of the volume level contained within the chamber 70 on the graduations 16. A port 88 is provided through the bottom 28 for access into the main part of the chamber 70.

The partition 66 separates the vacuum control means from the second cavity 64. However, the partition 66 does not extend all the way up to the top 90 in order that the vacuum control will be in communication with the remainder of the system. The vacuum control includes an inlet straw 92. The inlet straw 92 extends from the upper portion of the container down to near the bottom 94. Water is placed in the area set off by the partition 66 to provide a specific head. When vacuum in the container 10 is sufficient to overcome the head pressure, air is sucked in through straw 92 to relieve the excess vacuum. A cap 96 having slots 98 is fixed to the end of the straw 92 to break up the incoming air bubbles. The sound of these bubbles is psychologically bothersome to the patient and the cap helps to quiet the device.

At the upper end of the straw 92, an adaptor tube 100 is positioned to receive the straw. The adaptor tube 100 is fixed into the bottom of a container 102. The container 102 provides an easy pour access for filling the vacuum control through the straw 92. To prevent plugging of the vacuum control and to help eliminate the sound of air bubbles in the system, a loose-fitting cap 104 is positioned over the container 102. Of course, the cap 104 is removed for the purpose of filling the vacuum control.

Figure 2:
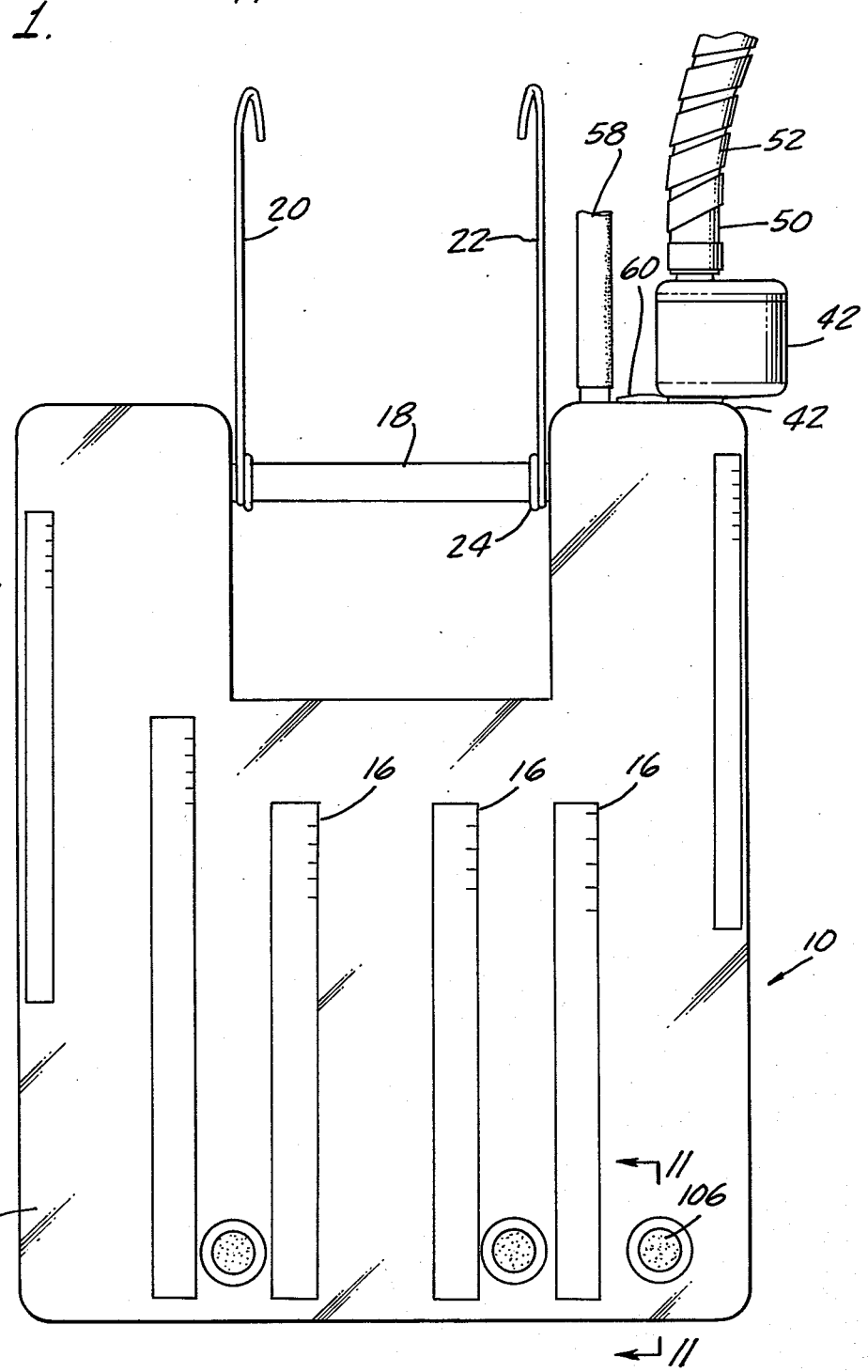
FIG. 2 is a front elevation of a device of the present invention.
Figure 11:
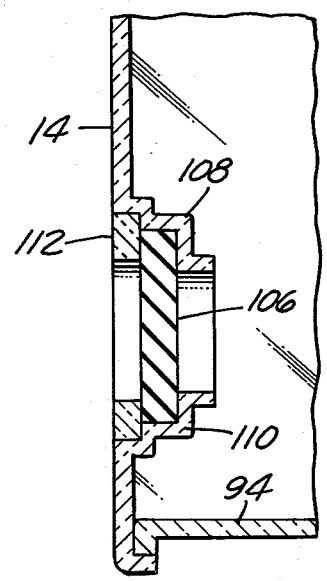
FIG. 11 is a cross-sectional elevation taken along line 11—11 of FIG. 2.

In the front plate 14, access seals 106 are employed as can best be seen in FIGS. 2 and 11. The access seals 106 are rubber or other highly resilient material which will reseal after a hypodermic syringe has been inserted for withdrawal of fluid and then removed. To retain the seals 106, the front plate 14 includes cylindrical cavities 108 having a shoulder 110. A retainer ring 112 is then bonded to the front plate 14 to prevent the seal 106 from popping out.

Thus, a device has been disclosed which provides a pleural drainage system having a water seal adjacent the inlet tube, a back flow preventer, vacuum control, and an accurately graduated container for holding the pleural discharge. While embodiments and applications of this application have been shown and described, it would be apparent to those skilled in the art that many more modifications are possible without departing from the inventive concepts herein. The invention, therefore, is not to be restricted except by the spirit of the appended claims.

What is claimed is:

1. A pleural drainage system, comprising
    a container having a first cavity, a second cavity, and a wall therebetween, said wall having a port, the lower edge of said port defining a first level, said port allowing unrestricted fluid communication above said first level between said first and second cavities;
    an inlet tube extending downwardly into said first cavity to an opening at a second level below said first level;
    a third cavity in said inlet tube, said third cavity having a volume greater than the volume of said first cavity below said first level; and
    a vacuum source above said first level.

2. A pleural drainage system, comprising
    a container having a first cavity, a second cavity positioned adjacent and extending below said first cavity, and a wall therebetween, said wall having a port, the lower edge of said port defining a first level, said port allowing unrestricted fluid communication above said first level from said first cavity to said second cavity between said first and second cavity;
    an inlet tube extending downwardly into said first chamber to an opening at a second level below said first level;
    a third cavity in said inlet tube, said third cavity having a volume exceeding the volume of said first cavity below said first level, said third cavity being positioned above said first level; and
    a vacuum source above said first level in said first cavity and in communication with said second cavity through said port.

* * * * *